United States Patent [19]

Haddad et al.

[11] Patent Number: 5,043,517
[45] Date of Patent: Aug. 27, 1991

[54] UPGRADING LIGHT OLEFIN FUEL GAS IN A FLUIDIZED BED CATALYST REACTOR AND REGENERATION OF THE CATALYST

[75] Inventors: James H. Haddad, Princeton Junction; Mohsen N. Harandi, Lawrenceville; Hartley Owen, Belle Mead, all of N.J.

[73] Assignee: Mobil Oil Corporation, Fairfax, Va.

[21] Appl. No.: 428,715

[22] Filed: Oct. 30, 1989

[51] Int. Cl.$^5$ .............................................. C07C 2/12
[52] U.S. Cl. .................................. 585/533; 585/520; 502/42; 502/44
[58] Field of Search .................. 585/520, 533; 502/42, 502/44

[56] References Cited

U.S. PATENT DOCUMENTS

| | | | |
|---|---|---|---|
| 4,159,239 | 6/1979 | Schwartz | 502/42 |
| 4,211,636 | 7/1980 | Gross et al. | 502/42 |
| 4,304,659 | 12/1981 | Pratt et al. | 208/113 |
| 4,453,323 | 6/1984 | Nassir | 502/42 |
| 4,746,762 | 5/1988 | Avidan et al. | 585/533 |
| 4,822,477 | 4/1989 | Avidan et al. | 208/49 |
| 4,859,308 | 8/1989 | Harandi et al. | 208/49 |
| 4,874,503 | 10/1989 | Herbst et al. | 585/533 |
| 4,926,003 | 5/1990 | Harandi et al. | 585/533 |
| 4,926,004 | 5/1990 | Pelrine et al. | 585/530 |
| 4,939,314 | 7/1990 | Harandi et al. | 585/533 |

Primary Examiner—Anthony McFarlane
Attorney, Agent, or Firm—Alexander J. McKillop; Charles J. Speciale; L. G. Wise

[57] ABSTRACT

Process for the continuous conversion of light olefin gas feed containing ethene, propene and butene to produce heavier hydrocarbons by contacting the light olefin feed in a fluidized bed reaction zone with a medium pore molecular sieve zeolite catalyst under oligomerization conditions to convert the light olefin feed to heavier hydrocarbons. The catalytic reaction causes the conversion of the light olefins to heavier hydrocarbons, the deposition of coke by-product on the catalyst and the absorption of hydrocarbon product on the catalyst. The deposited coke causes the partial deactivation of the catalyst. A portion of the partially deactivated catalyst containing deposited coke and absorbed hydrocarbon product is continuously withdrawn from the reaction zone and transferred to a catalyst stripping zone in which the catalyst is contacted with an inert stripping gas to remove the absorbed hydrocarbons from the catalyst. The stripped catalyst containing deposited coke is withdrawn from the stripping zone and transferred to a catalyst regeneration zone in which the catalyst is maintained in a fluidized bed and contacted with an oxygen containing gas to effect combustion of the coke and removal of the coke from the catalyst and regeneration of the catalyst. The regenerated catalyst containing a minor amount of residual carbon is withdrawn from the regeneration zone and introduced to the reaction zone and contacted with fresh light olefin feed. The careful control of the operating conditions in the regeneration zone provides removal of substantially all of the coke deposits at relatively low temperatures and an effluent flue gas with a low carbon monoxide content and low water content.

30 Claims, 3 Drawing Sheets

UPGRADING LIGHT OLEFIN FUEL GAS IN A FLUIDIZED BED CATALYST REACTOR AND REGENERATION OF THE CATALYST

CROSS-REFERENCED TO RELATED APPLICATIONS

This application is related to Avidan and Owen U.S. Ser. No. 006,407 filed Jan. 23, 1987, now U.S. Pat. No. 4,746,762, which is assigned to applicants' assignee and which is incorporated herein by reference thereto.

FIELD OF THE INVENTION

The present invention relates to a catalytic process for upgrading light olefin gas to heavier hydrocarbons and to the regeneration of the catalyst. In particular, it provides a continuous process for oligomerizing ethene-containing olefinic light gas feedstock, optionally containing propene and butene or other lower alkenes, to produce $C_4+$ hydrocarbons, such as olefinic liquid fuels, isobutane, aromatics and other useful products and to an efficient method for the continuous regeneration of the catalyst.

The present invention particularly relates to an improved process for controlling the temperature in the catalyst regeneration zone where an oxygen containing gas is contacted with partially deactivated catalyst to obtain a regenerated catalyst having a low carbon content and a regeneration zone effluent gas low in carbon monoxide and water content.

Ethene (ethylene, $C_2H_4$)-containing gases, such as petroleum cracking offgas, are useful feedstocks herein.

BACKGROUND OF THE INVENTION

The fluid catalytic cracking of hydrocarbons in modern refinery operations produce large amounts of $C_4-$ fuel gas of little or no gasoline product value.

Developments in zeolite catalysis and hydrocarbon conversion processes have created interest in utilizing olefinic feedstocks for producing $C_4+$ gasoline, diesel fuel, etc. In addition to basic chemical reactions promoted by ZSM-5 type zeolite catalysts, a number of discoveries have contributed to the development of new industrial processes. These are safe, environmentally acceptable processes for utilizing feedstocks that contain lower olefins, especially $C_2-C_4$ alkenes.

Conversion of $C_2-C_4$ alkenes and alkanes to produce aromatics-rich liquid hydrocarbon products were found by Cattanach U.S. Pat. No. 3,760,024 and Yan et al U.S. Pat. No. 3,845,150 to be effective processes using the ZSM-5 type zeolite catalysts. In U.S. Pat. Nos. 3,960,978 and 4,021,502, Plank, Rosinski and Givens disclose conversion of $C_2-C_5$ olefins, alone or in admixture with paraffinic components, into higher hydrocarbons over crystalline zeolites having controlled acidity. Garwood et al have also contributed to the understanding of catalytic olefin upgrading techniques and improved processes using zeolite catalyst as in U.S. Pat. Nos. 4,150,062, 4,211,640 and 4,227,992. The above-identified disclosures are incorporated herein by reference.

Conversion of lower olefins, especially ethene and propene over HZSM-5 is effective at moderately elevated temperatures and pressures. The conversion products are sought as liquid fuels, especially the $C_4+$ aliphatic and aromatic hydrocarbons. Product distribution for liquid hydrocarbons can be varied by controlling process conditions, such as temperature, pressure and space velocity. Gasoline ($C_5-C_{10}$) is readily formed at elevated temperature (e.g., up to about 510° C.) and moderate total pressure from ambient to about 5500 KPa (0 to 795 psig), preferably about 250 to 2900 KPa (36 to 419 psig). The olefin feed partial pressure is preferably in the range of 10 to 80 psia. Olefinic gasoline can be produced in good yield and may be recovered as a product or fed to a low severity, high pressure reactor system for further conversion to heavier distillate-range products. Distillate mode operation can be employed to maximize production of $C_{10}+$ aliphatics by reacting the lower and intermediate olefins at high pressure and moderate temperature. Operating details for typical "MOGD" oligomerization units are disclosed in U.S. Pat. Nos. 4,456,779, 4,497,968 (Owen et al.) and 4,433,185 (Tabak), incorporated herein by reference. At moderate temperature and relatively high pressure, the conversion conditions favor distillate-range product having a normal boiling point of at least 165° C. (330° F.). Lower olefinic feedstocks containing $C_2-C_6$ alkenes may be converted selectively; however, the low severity distillate mode conditions do not convert a major fraction of ethene. While propene, butene-1, and others may be converted to the extent of 50% to 95% in the lower severity moderate temperature distillate mode, only about 10% to 30% of the ethene component will be converted using HZSM-5 or similar acid zeolites. Many feedstocks of commercial interest, such as FCC light gas, dehydrogenation products, ethane cracking by-product, etc., contain both ethene and hydrogen along with $H_2S$ and light aliphatics.

SUMMARY OF THE INVENTION

The present invention relates to a refinery process for the production of gasoline boiling range hydrocarbons which comprises the steps of fractionating a crude oil feed stream into $C_4-$, light distillate, naphtha and atmospheric resid streams; passing the atmospheric resid or a fraction of it such as a vacuum gas oil stream into a fluidized catalytic cracking zone (FCC) which includes a fractionating column and producing an overhead $C_4-$ olefinic hydrocarbon fuel gas vapor stream; and contacting the $C_4-$ olefinic hydrocarbon with a zeolite catalyst under oligomerization process conditions to form $C_5+$ hydrocarbons. The $C_5+$ hydrocarbons are suitable gasoline blending stock.

In accordance with the present invention it has been found that $C_2$ to $C_4$ olefinic light gas can be upgraded to liquid hydrocarbons rich in gasoline containing aromatics, olefins and paraffins by catalytic conversion in a fluidized bed of solid acid zeolite catalyst under oligomerization reaction conditions in a single pass or with recycle of gas product and with continuous regeneration of the catalyst. This technique is particularly useful for upgrading FCC light gas, which usually contains significant amounts of ethene, propene, $C_1-C_3$ paraffins and hydrogen produced in cracking heavy petroleum oils or the like. By upgrading the by-product light gas, the gasoline yield of FCC units can be significantly increased.

An improved process has been found for continuous conversion of $C_2-C_4$ olefin-containing feedstocks to heavier hydrocarbon products of higher octane value wherein the feedstock is contacted at elevated temperature with a fluidized bed of zeolite catalyst under oligomerization conversion conditions and the catalyst is continuously regenerated. The improvement comprises maintaining the fluidized catalyst bed in a vertical reactor column by passing feedstock gas upwardly through the reaction zone, and withdrawing a portion of coked catalyst from the reaction zone, stripping the catalyst with an inert gas, oxidatively regenerating the withdrawn catalyst and returning regenerated catalyst to the reaction zone at a sufficient rate to control catalyst activity at a desired value.

The present invention is particularly useful for upgrading FCC light gas, which usually contains significant amounts of ethene, ethene and propene or propene and butene.

The operation of the catalyst regeneration zone is an important feature of the present invention.

The coke containing catalyst is contacted with an oxygen containing regeneration gas at elevated temperature to effect combustion of the coke deposits to remove the coke from the catalyst. The contacting is carried out in a fluidized dense catalyst phase in the lower portion of the regeneration zone. The oxygen containing regeneration gas is passed upwardly through the regeneration zone at a sufficient rate to fluidize the catalyst and to provide sufficient oxygen to effect combustion and removal of the coke from the catalyst. The space above the fluidized dense catalyst phase contains partially spent regeneration gases and catalyst entrained by the upward flowing regeneration gas. This portion of the regeneration zone is referred to as the dilute catalyst phase. The catalyst entrained in the dilute catalyst phase is recovered by gas solid separation cyclones located in the upper portion of the regeneration zone and the catalyst is returned to the fluidized dense catalyst phase in the regenerator.

Flue gas comprising water, carbon dioxide, carbon monoxide and other gases, such as nitrogen and unreacted oxygen are removed from the upper portion of the regeneration zone. The regenerated catalyst is removed from a lower portion of the regenerator and returned to the reaction zone.

In the regeneration of the zeolite catalyst, it is desirable to burn a substantial amount of the coke from the catalyst such that the residual carbon content of the regenerated catalyst is less than 0.20 weight percent and preferably less than 0.05 weight percent of the catalyst. The zeolite catalyst having a substantially reduced coke content on recycle to the reaction zone has high activity and high selectivity to the desired products.

In the regeneration of the zeolite catalyst it is preferred to operate the regeneration zone under conditions such that the flue gas leaving the regeneration zone has a carbon monoxide concentration of 50 ppm or less so that after removal of catalyst fines, if desired, the flue gas can be discharged into the atmosphere without additional treatment. The CO reduction can be enhanced by the addition to the regeneration zone of small amounts of catalyst metals such as platinum.

In order to obtain the low carbon content on regenerated catalyst of 0.20 weight percent or less and a flue gas having a low carbon monoxide content, it is necessary to provide oxygen containing regeneration gas in a sufficient excess amount of about 1 to 18 mol % oxygen in the flue gas. In order to prevent physical damage to the catalyst and deactivation of the catalyst it is preferred to operate the fluidized dense catalyst phase of the regeneration zone at a temperature of less than 1000° F. and most preferably less than 935° F.

Physical damage and deactivation of the catalyst can occur at the regeneration temperatures in the presence of water which is a by-product of the combustion of the coke deposits. To prevent physical damage to the catalyst the water partial pressure in the regenerator should be below about 20 psia, preferably below 15 psia at regeneration temperatures of for example 950° F.

In an embodiment of the invention the temperature in the regenerator zone can be controlled within the desired ranges by the use of cooling coils in the fluidized dense catalyst phase of the regeneration zone. In order to maintain the mechanical integrity of the cooling coil, the cooling fluid, for example boiler feed water, can be preheated by heat exchange with the reactor effluent hydrocarbon gas product. During low coke through-put, for example during low catalyst through-put in the regenerator the regeneration gas fed to the regenerator can be heated in order to maintain the amount of heat available to heat the boiler feed water cooling fluid.

In another embodiment of the invention the temperature in the regeneration zone may be controlled by cooling the stripped partially deactivated catalyst before feeding the catalyst to the regeneration zone and by cooling the regeneration gas before feeding the regeneration gas to the regenerator.

The physical damage to the catalyst in the regenerator due to regeneration temperatures above about 1000° F. and water partial pressures above 15 psia, decreases the activity and shortens the life of the catalyst and requires the addition or replacement of catalyst at a higher rate in order to maintain the desired catalyst activity which results in a substantial increase in the cost of carrying out the process.

The residence time of the catalyst in the fluidized dense catalyst phase of the regeneration zone is in the range of 6 to 75 minutes, preferably 30 to 60 minutes to provide regenerated catalyst with a low level of residual carbon on the regenerated catalyst.

The fluidized catalytic conversion of light olefins to heavier hydrocarbons by contact with a medium pore molecular sieve zeolite catalyst under oligomerization conditions causes the conversion of the light olefins to heavier hydrocarbon product, the deposition of coke by-product on the catalyst and the absorption of hydrocarbon product on the catalyst. The coke deposition causes the partial deactivation of the catalyst. In order to overcome the catalyst deactivation it is necessary to remove the partially deactivated catalyst from the reactor and to remove the coke deposits from the catalyst. The coke deposits may contain high boiling nitrogen compounds which act as catalyst poisons. The coke deposits are removed in a regeneration zone by contacting the catalyst with an oxygen containing gas to effect combustion of the coke and removal of the coke.

The reactor throughput and/or the severity of the catalystic conversion reaction in the reaction zone are limited by the regeneration zone temperature and the heat removal capacity of the regenerator, since greater reactor throughput and/or severity increases the quantity of coke deposited on the catalyst that must be burned off in the regenerator to regenerate the catalyst. The operation of the regeneration zone at higher temperatures to accommodate higher reactor throughput or severity is undesirable because of excess physical damage to the catalyst.

Thus high temperatures in the catalyst regenerator and high heat removal capacity requirements of the regenerator are limiting factors in plant design and increase the cost and operation of the overall plant.

At catalyst regeneration temperatures in excess of 1000° F., the structure of the medium pore molecular sieve zeolite catalyst undergoes physical change at a fast rate, usually observable as a reduction in the surface area of the catalyst, which results in a substantial decrease in catalyst activity. This decrease in activity is particularly severe in the presence of moisture in the regenerator. Consequently, in order to avoid rapid catalyst deactivation, it is necessary to maintain the temperature in the regenerator below 1000° F. and to maintain the water content in the regenerator below 15 psia partial pressure.

An additional problem is to maintain the carbon monoxide content of the regenerator effluent gas below 50 ppm to meet the environmental requirements.

A large amount of coke deposit and a large amount of absorbed hydrocarbon product on the catalyst requires a large heat removal capacity in the catalyst regenerator to remove the heat of combustion. The heat removal capacity requirements can be reduced by efficient removal from the catalyst of the absorbed hydrocarbon product in a stripping zone prior to the regeneration of the catalyst and by carrying out the reaction process in a manner such that the coke deposits are not excessive.

The hot effluent gases from the catalyst regenerator, in an embodiment of the invention, are passed through a turbine expander, or through a heat exchanger to develop power to operate the compressor for the regeneration air feed to the catalyst regenerator.

ADVANTAGES

The process of the present invention because of the efficient stripping of hydrocarbon product from catalyst in the stripping zone substantially reduces the heat removal capacity requirements of the catalyst regeneration. The stripping of the hydrocarbon product can also substantially reduce hydrogen carry over from the reactor into the regeneration zone, which would form water, and thus reduce the water partial pressure in the regenerator. The stripped hydrocarbon product can be recovered and thereby increase product yield. The carrying out of the catalyst regeneration at relatively low temperatures and low water partial pressure, and at low water content in the effluent gases substantially increases catalyst life and regenerated catalyst activity.

The use of once through air as the regenerating gas in the catalyst regeneration zone assists in the control of the regeneration zone temperature, prevents build up of undesirable combustion products such as water in the regeneration zone, and substantially simplifies the design cost and cost of operation of the regeneration zone as compared to a process that recycles the effluent regenerator gas to the regeneration zone.

The use of the stripper zone to remove absorbed hydrocarbons from the partially deactivated catalyst reduces the heat removal capacity requirements of the regeneration zone typically by 20 to 40% and can increase the yield of hydrocarbon product. It is a further advantage of the process of the present invention that the catalyst residence time in the regeneration vessel can be substantially reduced as compared to the residence times employed in other processes. Thus it is possible to operate the process of the present invention at reduced catalyst inventory in the regenerator vessel which substantially reduces the catalyst exposure time to water and high temperatures. This minimizes catalyst deactivation rate.

The catalyst regenerator typically operates at 100 to 250 psig, preferably 150 to 200 psig. Therefore, even a relatively low water concentration in the effluent gas corresponds to a relatively high water partial pressure in the regeneration zone, which makes the water partial pressure in the regeneration zone particularly difficult to control at the necessary low value. In order to reduce the water partial pressure in the regenerator, the regeneration air after it has been pressurized can be cooled to remove water prior to being fed to the regeneration zone.

The effluent gas from the catalyst regenerator can be fed to an expander or to a heat exchanger to generate power to develop electricity to provide power to operate a compressor to increase the pressure of regeneration air to the operating pressure in the regenerator. Added advantages of the process and apparatus of the present invention are to use as regeneration air, the regeneration air feed to the FCC regenerator, and to feed the regeneration effluent gases from the instant process which contain excess oxygen to the FCC regenerator and to recover regenerator gas effluent catalyst fines from the instant process in the FCC regenerator fines recovery system.

Further, the use of a high flow rate of regeneration air to the regenerator prevents any sudden rise in the regeneration zone temperature which results in a more stable regenerator operation.

BRIEF DESCRIPTION OF THE DRAWINGS

The FIG. 1 of the drawings is a schematic representation of a fluidized bed catalyst reaction zone process and apparatus including an improved catalyst stripper vessel and stripping process and a catalyst regenerator employing a fluidized bed regeneration zone comprising cooling coils and a preheater for the regeneration gas.

The FIG. 2 of the drawings is a schematic representation of a fluidized bed catalyst reaction zone process and apparatus similar to that of FIG. 1 including an improved catalyst stripper vessel and stripping process and a catalyst regenerator. The stripped catalyst is cooled prior to introducing the catalyst in the regenerator and the regeneration gas is cooled to control the regeneration temperature and to remove water prior to introducing the regeneration gas to the regenerator.

Figure 3:
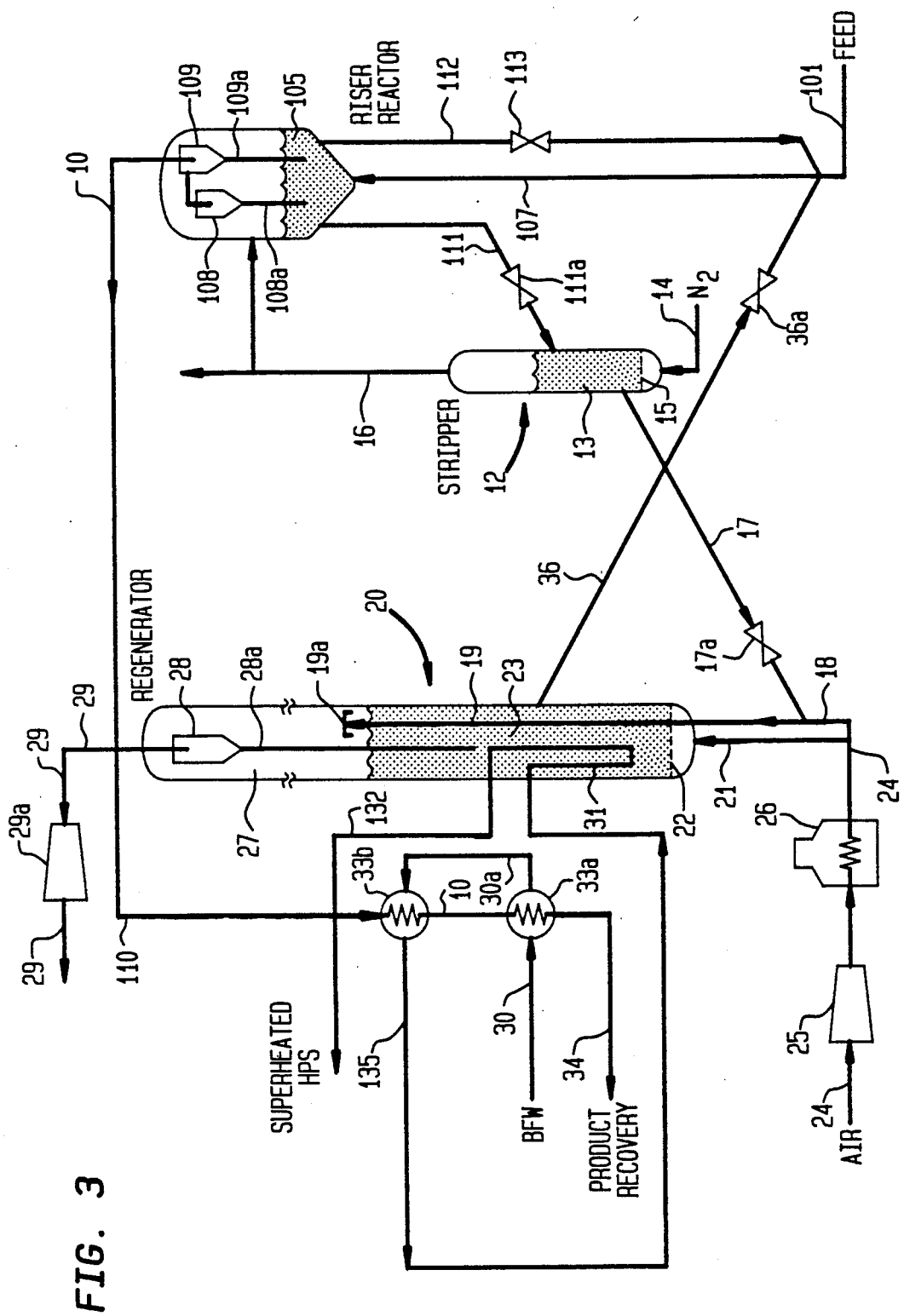

The FIG. 3 of the drawings is a schematic representation of a riser reactor catalyst reaction zone process and apparatus, including an improved catalyst stripper vessel and stripping process and a catalyst regenerator employing a fluidized bed regeneration zone comprising cooling coils and a preheater for the regeneration gas.

OBJECTS OF THE INVENTION

An object of the present invention is to provide a novel economical process for the catalytic conversion of a hydrocarbon feed containing light olefins, including ethene, propene and butene to produce heavier hydrocarbons by contacting the light olefin feed in a fluidized bed reaction zone with a medium pore molecular sieve zeolite catalyst under oligomerization conditions to convert the light olefin feed to $C_4^+$ heavier hydrocarbons and to a process for efficiently and economically regenerating the catalyst in a fluidized bed catalyst regeneration zone.

It is another object of the present invention to provide an improved method for stripping hydrocarbons from partially deactivated catalyst prior to regeneration of the catalyst. It is another object of the present invention to provide an improved process for the high pressure regeneration of the catalyst at relatively low temperature, and low water partial pressure.

It is still another object of the present invention to provide an efficient and economical method for the regeneration of the catalyst in a catalyst regeneration zone under conditions of combustion of the coke on the catalyst to have the regeneration effluent gases contain a low concentration of carbon monoxide.

It is still another object of the present invention to provide an efficient economical method of regenerating partially deactivated medium pore molecular sieve zeolite catalyst containing coke deposits in a fluidized catalyst bed regeneration zone under conditions of relatively low temperature and low water partial pressure in the regeneration zone and low water content in the regeneration zone effluent gas such that the useful life of the regenerated catalyst is increased and the activity of the regenerated catalyst is increased.

DETAILED DESCRIPTION OF THE INVENTION

The present invention utilizes conventional petroleum refining steps including fractionation, coking and fluidized catalytic cracking and a novel zeolite catalyst oligomerization process to upgrade the olefinic $C_4^-$ process streams. A gasoline boiling range aliphatic hydrocarbon product stream is produced from the olefinic $C_4^-$ stream from the fluidized catalytic cracking process step.

In accordance with the present invention crude oil feed is subjected to distillation to separate several hydrocarbon streams including a light gas, a gasoline boiling range light distillate naphtha, a middle distillate, a vacuum gas oil and a bottoms or reduced crude stream.

The naphtha stream is hydrotreated to remove sulfur and nitrogen compounds and then fed to a catalytic reforming zone wherein the octane value of this stream is increased, the concentration of aromatic hydrocarbons is increased and hydrogen is produced as a by-product.

The middle distillate stream is hydrotreated to produce products such as kerosene and jet fuel.

The vacuum gas oil is fed to a fluidized catalytic cracking zone (FCC) in which there is produced a light gasoline boiling range distillate, an olefinic $C_4^-$ stream containing $C_1$ to $C_4$ olefins and paraffins, and a heavy distillate. The FCC unit includes a fluidized bed molecular sieve catalytic cracker and a catalyst regenerator. The molecular sieve catalyst is continuously regenerated in the regenerator by oxidatively removing coke deposits from the catalyst by burning the coke with air regeneration gas.

The reduced crude may be fed into a coker unit where more light olefins are produced. The reduced crude may also be subjected to processing steps such as propane deasphalting, hydrocracking, etc.

The olefinic $C_4^-$ stream or a fraction of it containing $C_1$ to $C_4$ olefins and paraffins made, for example, in a catalytic cracker and/or coker in accordance with the process of the present invention are fed to a fluidized zeolite catalyst reaction zone in a fluid bed reactor. The fluid bed reactor containing the zeolite catalyst is operated under oligomerization process conditions to convert the $C_4^-$ olefin hydrocarbons to $C_5^+$ aliphatic hydrocarbons.

The catalyst in the fluid bed reactor is continuously withdrawn and regenerated in a catalyst regeneration zone. Prior to carrying out the regeneration step the catalyst is preferably contacted in a stripping zone with an inert stripping gas such as nitrogen to remove hydrocarbons absorbed on the catalyst.

The present invention more particularly relates to a process for the continuous conversion of light olefin gas feed containing ethene, propene and/or butene to produce heavier hydrocarbons by contacting the light olefin feed in a fluidized bed reaction zone with a medium pore molecular sieve zeolite catalyst under oligomerization conditions to convert the light olefin feed to heavier hydrocarbons.

A portion of the catalyst is continuously withdrawn from the reaction zone and transferred to a catalyst stripping zone to remove absorbed hydrocarbons from the catalyst.

The stripped catalyst containing deposited coke is withdrawn from the stripping zone and transferred to a catalyst regeneration zone and contacted with an oxygen containing gas to effect combustion of the coke and removal of the coke from the catalyst and regeneration of the catalyst. The regenerated catalyst is withdrawn from the regeneration zone and introduced to the reaction zone and contacted with fresh light olefin feed.

DESCRIPTION OF LIGHT OLEFIN FEED

A preferred light olefin gas feedstock contains $C_2$ to $C_4$ alkenes (mono-olefins), wherein the total $C_2$-$C_4$ alkenes are in the range of 10 to 40 wt. %. Non-deleterious components, such as methane, $C_3$-$C_4$ paraffins and inert gases, may be present. Some of the paraffins may be converted to $C_4^+$ hydrocarbons depending on the reaction conditions and catalyst employed. A particularly useful feedstock is a light gas by-product of FCC gas oil cracking units containing typically 10-40 mol % $C_2$-$C_4$ olefins and 5-35 mol % $H_2$ with varying amounts of $C_1$-$C_3$ paraffins and inert gas, such as $N_2$. The feedstock can contain primarily ethene, ethene and propene or propene and butene.

The olefinic feedstream may be enriched by addition of propene to increase the production of $C_4^+$ product. Propene or butene containing streams, such as $C_3$-$C_4$ LPG and various refinery fractions can be employed as the olefinic feedstock. Alcohol, for example methanol, containing etherification debutanizer overhead such as from the methyl tertiary butyl ether (MTBE) process is also a desired feed. The MTBE overhead stream contains lower olefins and methanol.

Upgrading of olefins by the addition of paraffins in fluidized bed cracking and oligomerization units is taught by Owen et al in U.S. Pat. No. 4,090,949. This technique is particularly useful for operation with a fluidized catalytic cracking (FCC) unit to increase overall production of liquid product in fuel gas limited petroleum refineries. Light olefins and some of the light paraffins, such as those in FCC fuel gas, can be converted to valuable $C_4^+$ hydrocarbon product in a fluid-bed reactor containing a zeolite catalyst. In addition to fuel gas upgrading, the load to the refinery fuel gas plant is decreased considerably. This allows operation of the FCC unit at higher throughput and/or higher severity in fuel gas limited refineries.

The light olefin feed gas is described in more detail in the Table 1 below.

TABLE 1

| Mole % | Broad | Intermediate | Preferred |
|---|---|---|---|
| $H_2$ | 0 to 50 | 0 to 30 | 0 to 10 |
| Ethene | 0 to 90 | 0 to 40 | 0 to 20 |
| Propene | 1 to 99 | 1 to 80 | 3 to 40 |
| Butene | 0 to 99 | 0 to 80 | 1 to 40 |
| Methanol | 0 to 20 | 0 to 10 | 0 to 3 |

DESCRIPTION OF CATALYSTS

Recent developments in zeolite technology have provided a group of medium pore siliceous materials having similar pore geometry. Most prominent among these intermediate pore size zeolites is ZSM-5, which is usually synthesized with Bronsted acid active sites by incorporating a tetrahedrally coordinated metal, such as Al, Ga, B or Fe, within the zeolitic framework. These medium pore zeolites are favored for acid catalysis; however, the advantages of ZSM-5 structures may be utilized by employing highly siliceous materials or crystalline metallosilicate having one or more tetrahedral species having varying degrees of acidity. ZSM-5 crystalline structure is readily recognized by its X-ray diffraction pattern, which is described in U.S. Pat. No. 3,702,866 Argauer et al, incorporated by reference.

The oligomerization catalysts preferred for use herein include the medium pore (i.e., about 5-7A) shape-selective crystalline aluminosilicate zeolites having a silica-to-alumina ratio of at least 12, a constraint index of about 1 to 12 and acid cracking activity of about 1-200. In the fluidized bed reactor the coked catalyst may have an apparent activity (alpha value) of about 1 to 80 under the process conditions to achieve the required degree of reaction severity. Representative of the ZSM-5 type zeolites are ZSM-5, ZSM-11, ZSM-12, ZSM-22, ZSM-23, ZSM-35, and ZSM-38. ZSM-5 is disclosed in U.S. Pat. No. 3,702,886 and U.S. Pat. No. Re. 29,948. The ZSM-5 and ZSM-12 catalyst are preferred. Other suitable zeolites are disclosed in U.S. Pat. Nos. 3,709,979, 3,832,449, 4,076,979, 3,832,449, 4,076,842, 4,016,245 and 4,046,839, 4,414,423, 4,417,086, 4,517,396 and 4,542,251. The disclosures of these patents are incorporated herein by reference. While suitable zeolites having a coordinated metal oxide to silica molar ratio of 20:1 to 200:1 or higher may be used, it is advantageous to employ a standard ZSM-5 having a silica alumina molar ratio of about 25:1 to 70:1, suitably modified. A typical zeolite catalyst component having Bronsted acid sites may consist essentially of aluminosilicate ZSM-5 zeolite with 5 to 95 wt. % silica and/or alumina binder.

Certain of the ZSM-5 type medium pore shape selective catalysts are sometimes known as pentasils. In addition to the preferred aluminosilicates, the borosilicate, ferrosilicate and "silicalite" materials may be employed. It is advantageous to employ a standard ZSM-5 having a silica:alumina molar ratio of 25:1 to 70:1 with an apparent alpha value of 1-80 to convert 60 to 100 percent, preferably at least 70%, of the olefins in the feedstock to heavier hydrocarbons.

ZSM-5 type pentasil zeolites are particularly useful in the process because of their regenerability, long life and stability under the extreme conditions of operation. Usually the zeolite crystals have a crystal size from about 0.01 to over 2 microns or more, with 0.02-1 micron being preferred. In order to obtain the desired particle size for fluidization, the zeolite catalyst crystals are bound with a suitable inorganic oxide, such as silica, alumina, etc. to provide a zeolite concentration of about 5 to 95 wt. %. A preferred catalyst comprises 25 to 35% H-ZSM-5 catalyst contained within a silica-alumina matrix binder and having a fresh alpha value of less than 80.

Particle size distribution can be a significant factor in achieving overall homogeneity in the fluidized bed. It is desired to operate the process with particles that will mix well throughout the bed. Large particles having a particle size greater than 250 microns should be avoided, and it is advantageous to employ a particle size range consisting essentially of 1 to 150 microns. Average particle size is usually about 20 to 100 microns, preferably 40 to 80 microns. Particle distribution may be enhanced by having a mixture of larger and smaller particles within the operative range, and it is particularly desirable to have a significant amount of fines. Close control of distribution can be maintained to keep about 10 to 25 wt. % of the total catalyst in the reaction zone in the size range less than 32 microns. This class of fluidizable particles is classified as Geldart Group A.

The present process can be carried out in dense fluidized beds, fluidized beds having a turbulent fluidization regime and in riser reactors.

REACTION PRODUCTS

Hydrocarbon Products

The contacting of the light olefin gas feed over the zeolite catalyst in accordance with the present invention produces the following products.

The desired products are $C_4$ to $C_{15}$ hydrocarbons, typically $C_5$ to $C_9$ hydrocarbons which will comprise at least 50 wt. % of the recovered product, preferably 70% or more. While olefins may be a predominant fraction of the $C_4+$ reaction effluent, up to 99% butenes, pentenes, hexenes, heptenes, octenes, nonenes, $C_{10}+$ olefins and cyclo olefins and their isomers, it is desired to upgrade the feedstock to high octane gasoline containing aromatics, preferably at least 10% by weight.

Unreacted, or ethene, propene and butene formed in the reaction can be recycled to the zeolite catalyst reactor.

The ethene, propene and butene in the light olefin feed are converted in an amount of 20 to 100, preferably 60 to 100 and more preferably 80 to 100 wt. % of the feed.

The catalyst in the reaction zone absorbs hydrocarbons. The absorbed hydrocarbons comprise a mixture of reaction feed, reaction product and intermediate hydrocarbon products. These hydrocarbon are stripped from the catalyst in the stripper vessel prior to the regeneration of the catalyst.

BY-PRODUCT COKE

An undesirable by-product of the catalytic reaction is the formation of coke which deposits on the catalyst and which after a period of time builds up and partially deactivates the catalyst. The term coke as used herein is intended to mean the by-product material that deposits and builds up on the catalyst and which comprises non volatile carbonaceous material consisting primarily of high boiling nitrogen compounds and highly condensed aromatic hydrocarbons typically containing about 4 to 10 wt. % hydrogen. The combustion of the coke in the catalyst regeneration zone leaves a small residual amount of carbon on the regenerated catalyst.

REACTOR

Fluidized Bed Reactor

The process of the present invention using a ZSM-5 type zeolite catalyst is carried out at temperatures of about 400°-950° F. (204°-510° C.) preferably 500°-750° F. (260°-399° C.) and more preferably at 600°-750° F. (316°-399° C.).

The pressure at which the reaction is carried is an important perimeter of the invention. The process can be carried out at pressures of 50-500 psig (445-3550 kPa), preferably 100-400 psig (790-2860 kPa) and more preferably at 100-250 psig (790 to 1800 kPa). the weight hourly space velocity (WHSV) of the light olefin feed is an important perimeter of the process. The principle reactants in the process are the ethene, ethene and propene or propene and butene constituents of the light olefin gas feed and the WHSV are given in terms of these olefin components. The light olefins in the feed WHSV can be 0.1 to 50, preferably 0.1 to 5 and more preferably 0.5 to 1.5.

The fluidizing gas velocity through the catalyst bed is 0.3 to 3 ft/sec (0.09 to 0.91 m/sec), preferably 0.5 to 2 ft/sec (0.15 to 0.61 m/sec) and more preferably 0.7 to 1.3 ft/sec (0.21 to 0.40 m/sec). The fluidizing gas comprises the light olefin feed and the hydrocarbon products as they are formed.

Catalyst particles are disengaged from the hydrocarbon gas product in the top dilute phase of the reaction zone in one or more gas-solid separation cyclones and the separated catalyst is returned to the catalyst bed. The hydrocarbon product gas is removed from the top of the reactor at about the same temperature as the reaction zone temperature and is taken for further processing and/or for heat exchange with process streams.

The oligomerization conversion reaction converts a portion of the hydrocarbon feed to undesirable coke by-product which coke deposits on the catalyst and as the coke deposits build up on the catalyst partially deactivates the catalyst. Also, during the reaction hydrocarbon products is absorbed on the catalyst which if not recovered can represent a loss of yield of product to the process, and increases the heat removal capacity requirements of the catalyst regenerator.

The process conditions are controlled to optimize yield of $C_5$-$C_9$ aliphatic hydrocarbons. It is understood that aromatic and light paraffin production is promoted by the zeolite catalyst having a high concentration of bronstead acid reaction cite. Accordingly, an important criteria is selecting and maintaining catalyst inventory to provide either fresh catalyst having acid activity or by controlling catalyst deactivation and regeneration rates to provide an apparent average alpha value of 1-80.

The fluidized bed in the reactor can typically have a diameter of 3 to 15 ft (0.91 to 4.57 m), typically 4 to 10 ft (1.22 to 3.05 m) and a height of 5 to 50 ft (1.52 to 15.24 m), typically 15 to 30 ft (4.57 to 9.14 m).

The average olefin feed residence time in the reactor fluidized bed reaction zone can be 3 to 80 seconds, typically about 15 to 25 seconds.

The use of the fluidized bed catalyst process permits the reactor to be operated at low pressure drop. An important advantage of the process is the close temperature control and reactor stability that is made possible by the fluidized bed operation, wherein the uniformity of conversion temperature can be maintained within close tolerances.

In a typical process, a propene and butene rich $C_2$ to $C_4$ olefin feedstock is converted in a catalytic reactor under oligomerization conditions of 600°-750° F. (260°-399° C.) temperature and under moderate pressure of 100-250 psig (790 to 1800 kPa) to produce a predominately liquid product consisting of $C_4{}^+$ aliphatic hydrocarbons rich in gasoline range olefins.

Riser Reactor

The hydrocarbon conversion reaction carried out in the riser reactor is similar to that carried out in the fluidized bed reactor. The process utilizes a ZSM-5 type zeolite catalyst and the conversion reaction is carried out primarily in the riser section of the reactor. The use of a small fluidized bed above the riser section of the reactor is optional, and when used some conversion can take place in this bed.

The reaction temperature in the riser section of the reactor is 400° to 950° F. (204° to 510° C.), preferably 500° to 750° F. (260° to 399° C.) and more preferably 600° to 750° F. (316° to 399° C.). The reaction pressure in the riser section of the reactor is 50 to 500 psig (445 to 3550 kPa), preferably 100 to 400 psig (790 to 2860 kPa) and more preferably 100 to 250 psig (790 to 1800 kPa). The weight hourly space velocity (WHSV) of the light olefin in the feed can be 0.5 to 100, preferably 2 to 10 and more preferably 4 to 6.

The transfer gas velocity in the riser section of the reactor is 5 to 100 ft/sec (1.5 to 30 m/sec), preferably 5 to 30 ft/sec (1.5 to 9.1 m/sec) and more preferably 10 to 20 ft/sec (3 to 6.1 m/sec).

The use of an upper fluidized bed is an alternative embodiment of the invention. The riser reactor can be operated with or without an upper fluidized bed.

The fluidizing gas velocity in the upper fluid bed section of the reactor, when the upper fluidized bed is used, can be 0.3 to 4 ft/sec (0.1 to 1.2 m/sec), preferably 1 to 3 ft/sec (0.3 to 0.9 m/sec) and more preferably 1 to 1.5 ft/sec (0.3 to 0.5 m/sec). The upper fluid bed section of the reactor is preferably operated as a turbulent regime fluidized bed.

The height of the riser section of the reactor can be 10 to 100 ft (3 to 30 m), preferably 20 to 60 ft (6 to 18 m). The diameter of the riser section can be 0.1 to 1 ft (0.03 to 0.3 m), typically 0.1 to 0.5 ft (0.03 to 0.15 m) in diameter. The fluidized bed above the riser section of the reactor, when used, can have a height of 5 to 30 ft (1.5 to 9.1 m), typically 5 to 20 ft (1.5 to 6.1 m) and a diameter of 1 to 30 ft (0.3 to 9.1 m), typically 2 to 6 ft (0.6 to 1.8 m). A portion of the catalyst in the upper fluidized bed can be recirculated through a catalyst recirculation line to enter the bottom of the riser section with the feed.

The olefin feed residence time in the riser reactor is typically 1 to 20, and preferably 3 to 10 seconds.

The operation of the riser reactor is otherwise generally similar to that of the fluidized bed reactor, for example, the process is carried out at about the same temperatures and pressures, and the coke deposition rates and hydrocarbon product absorption rates on the catalyst are about the same as those described in the fluidized bed reactor embodiment of the invention.

STRIPPING ZONE

In order to regenerate the catalyst and to remove the absorbed hydrocarbon product, a portion of the partially deactivated catalyst containing the deposited coke and absorbed hydrocarbon product is continuously withdrawn from, for example, the fluidized bed portion of the reactor and transferred to a catalyst stripping zone. About 5 to 50%/hr, preferably 7 to 20%/hr and more preferably 10 to 15%/hr of the catalyst inventory in the reactor is withdrawn for stripping and regeneration. The catalyst is withdrawn from the reactor at about the reaction zone temperature and pressure. The rate at which the catalyst is withdrawn depends on the olefin feed rate. Typically for an olefin feed rate of 10,000 lb/hr olefins the catalyst is withdrawn at a rate of 3000 lb/hr.

The partially deactivated catalyst contains 0.2 to 5 wt. % deposited coke, typically 1 to 4 wt. % coke, and more typically 1 to 3 wt. % coke. The partially deactivated catalyst also contains absorbed on the catalyst 0.1 to 2 wt. %, for example 0.1 to 1.5 wt. % and 0.1 to 1.0 wt. % intermediate hydrocarbons and hydrocarbon product.

The partially deactivated catalyst is transferred to the stripper vessel and is maintained in the stripper vessel as a fluidized bed in the stripping zone at a temperature of 200° to 950° F. (93° to 510° C.), preferably 300° to 750° F. (150° to 400° C.) and more preferably 500° to 700° F. (260° to 370° C.). The pressure in the stripping vessel is maintained at about plus or minus 20 psi (3 kPa) of the reactor pressure. The partially deactivated catalyst is maintained as a fluidized bed in the stripper zone by contact with an inert stripping gas such as nitrogen which is introduced at the bottom of the stripping vessel at a temperature of 10° to 900° F. (−12° to 480° C.), preferably 50° to 200° F. (10° to 94° C.) and more preferably at 50° to 100° F. (10° to 38° C.). The stripping gas is introduced to the stripper at a sufficient rate to maintain the fluidized bed. The stripping gas superficial velocity through the bed is 0.03 to 3 ft/sec (0.01 to 1 m/sec), preferably 0.1 to 1.5 ft/sec (0.03 to 0.45 m/sec), and more preferably 0.5 to 1.5 ft/sec (0.15 to 0.45 m/sec). The catalyst residence time in the stripper can be 5 to 500 sec, typically 60 to 150 sec.

The stripping gas can comprise an inert gas such as nitrogen, regenerator effluent gas or steam. However, nitrogen gas is preferred.

The partially deactivated catalyst in the stripping zone is stripped of substantially all of the hydrocarbon product, leaving on the catalyst substantially only the deposited coke. The stripped hydrocarbon product can be returned to the reactor vessel and/or processed for recovery.

The effluent gases from the stripping zone alternatively can be treated to separate the stripping gas, e.g. nitrogen, from the stripped hydrocarbon product. The separated nitrogen can be recycled to the stripping zone. The separated hydrocarbons can be returned to the reaction zone for further treatment or can be added to the effluent hydrocarbon product stream from the reactor.

The stripper vessel can be conveniently sized and have a diameter of 1/5 to 2 ft (0.06 to 0.61 m), typically ⅓ to 1 ft (0.1 to 0.3 m) and a height of 6 to 30 ft (1.8 to 9.1 m), typically 15 to 25 ft (4.6 to 7.6 m).

The stripping zone is separate from the fluidized catalyst bed in the reactor. The stripper vessel can be disposed external to the reactor vessel or can be placed within the fluidized bed in the reactor.

REGENERATOR

The stripped catalyst containing deposited coke is withdrawn from the stripping zone and is transferred to the catalyst regeneration zone in which the catalyst is maintained in a fluidized bed. The partially deactivated catalyst is contacted in the fluidized bed with an oxygen containing regeneration gas, such as air, to effect combustion of the coke deposited on the catalyst and removal of the coke from the catalyst and regeneration of the catalyst.

A suitable regeneration gas is air which contains about 21% oxygen and 79% nitrogen, because of its ready availability and low cost. However, a preferred regeneration gas is the air feed gas to the FCC catalyst regenerator.

A sufficient amount of the oxygen containing regenerating gas is fed to the bottom of the regenerator through a distribution plate to the regeneration zone to maintain a temperature in the regeneration zone of 700° to 1000° F. (371° to 538° C.), preferably 850° to 950° F. (454° to 510° C.), and more preferably 900° to 950° F. (482° to 510° C.) and to provide sufficient fluidizing gas to maintain the catalyst in a fluidized bed. The pressure in the regenerator is maintained at 50 to 300 psig (440 to 2150 KPa), preferably 100 to 250 psig (790 to 1800 kPa) and more preferably 150 to 200 psig (1130 to 1440 KPa) by pressurizing the regenerating gas before it is introduced into the regenerator. Preferably the pressure in the regenerator is maintained within about 20 psi of the pressure in the reactor, and more preferably within 10 psi of the pressure in the reactor, for example within about 0 to 5 psi of the pressure in the reactor. The fluidizing gas superficial velocity in the fluidized bed is 0.1 to 3 ft/sec (0.03 to 0.91 m/sec), preferably 0.1 to 1 ft/sec (0.03 to 0.3 m/sec), and more preferably 0.3 to 0.7 ft/sec (0.09 to 0.2 m/sec). The catalyst particles are disengaged from the fluidizing gas, including the combustion products of the coke and oxidizing gas, in the top dilute phase of the regeneration zone by one or more gas-solid separation cyclones and the separated catalyst is returned to the regeneration zone fluidized catalyst bed. The excess oxygen in the regenerating gas and the combustion products including carbon monoxide, carbon dioxide and water are removed from the regenerator as effluent gases. The effluent gases contain 0 to 2 wt. %, preferably 0 to 500 ppm and more preferably 0 to 50 ppm carbon monoxide; 1 to 20 mol. % oxygen, and preferably 1 to 10 mol. % oxygen and more preferably 5 to 10 mol. % oxygen. The partial pressure of the water in the regenerator is 1 to 20 psia, preferably 1 to 15 psia and more preferably 1 to 5 psia. The effluent gases also contain a small amount of catalyst fines in the amount of 0 to 5 wt. %, typically 0.05 to 2 wt. % and more typically 0.1 to 1.5 wt. % of the effluent gases, for example 0.05 to 1 wt. %.

The regenerator catalyst inventory is about 5–30 wt. %, typically 10 to 15 wt. % of the reactor catalyst inventory.

The effluent gases can conveniently be fed to a FCC catalyst regenerator unit in which the carbon monoxide is converted to carbon dioxide, the excess oxygen is burned and the catalytic particles and their heat content are recovered in the FCC catalyst regenerator flue gas heat recovery unit. The recovered catalyst can be added to the FCC process to enhance octane of the FCC reaction process.

The medium pore molecular sieve zeolite catalyst is regenerated in the regeneration zone by the combustion and removal of substantially all of the coke deposited on the catalyst. The average residence time of the catalyst in the regeneration zone is 6 to 75 minutes, typically 30 to 60 minutes and more typically 50 to 60 minutes. The regenerated catalyst is continuously withdrawn from the regeneration and is introduced to the reaction zone and contacted with fresh olefin feed. The regenerated catalyst contains only a small residual amount of carbon in the amount of 0.01 to 0.5 wt. %, preferably 0.01 to 0.20 wt. % and more preferably 0.01 to 0.05 wt. % based on the weight of catalyst.

PREFERRED EMBODIMENTS

Figure 1:
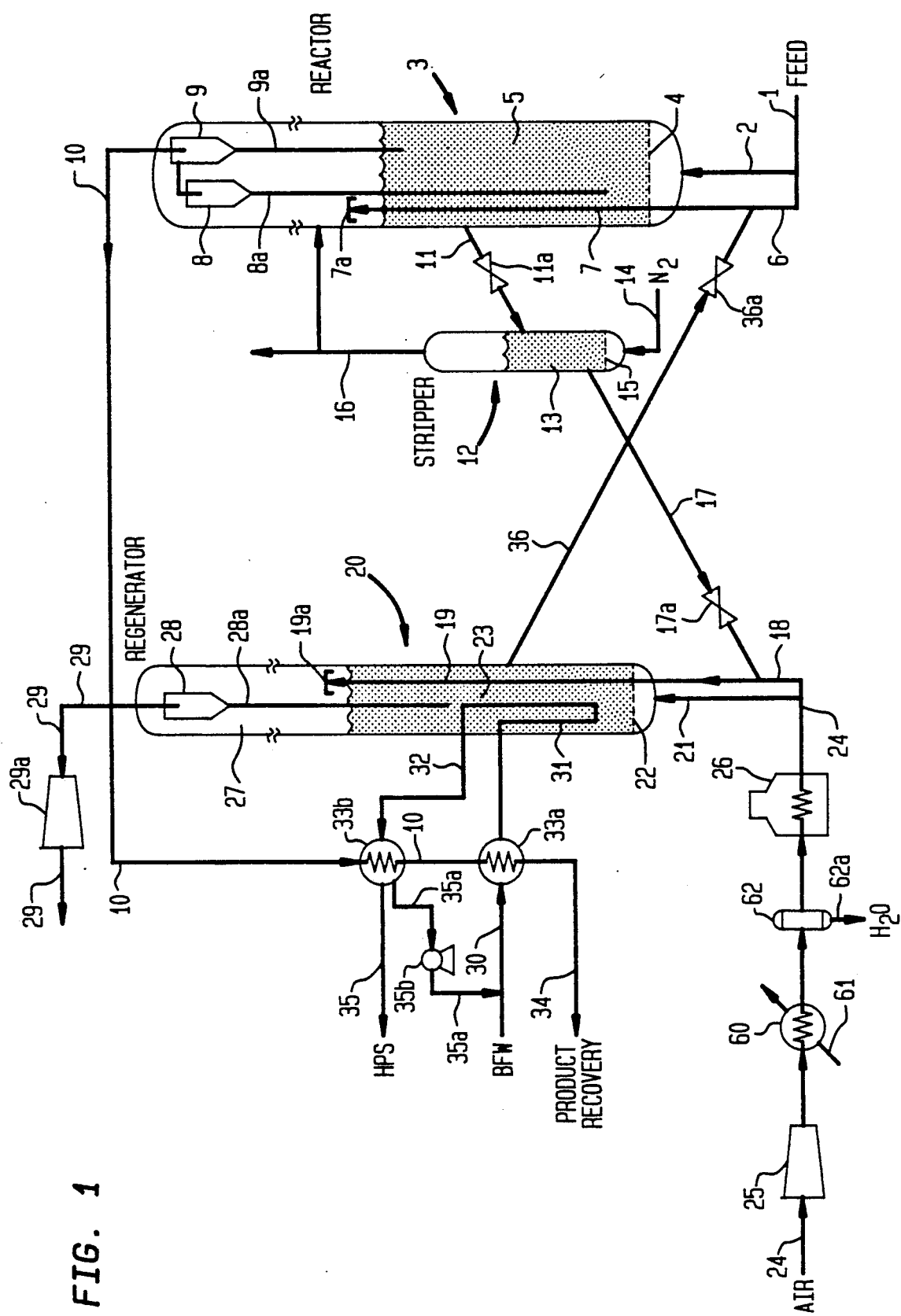

Referring to FIG. 1 of the drawings, a pressurized feed gas rich in $C_2$–$C_4$ olefins is fed through line 1 with the main flow being directed to the bottom inlet 2 of the reactor vessel 3 for distribution through grid 4 into fluidization zone 5. Here the olefin feed contacts the fluidized bed of finely divided catalyst particles. The remainder of the heated olefin feed gas is fed through line 6 to catalyst return riser conduit 7 in which it functions as a lift gas for the regenerated catalyst.

The reaction heat can be partially or completely removed from the fluidized bed reaction zone by using cold or only partially preheated olefin feed gas. Baffles may be added to the reaction vessel to control radial and axial mixing. Heat released from the reaction can be controlled by adjusting temperature in a known matter. The oligomerization reaction is carried out in the fluidized bed reaction zone at temperatures of 600° to 750° F. (316° to 399° C.) and at pressures of 100 to 250 psig (790 to 825 KPa). The light hydrocarbon feed is fed to the reactor at 0.5 to 1.5 WHSV, based on $C_2$ to $C_4$ olefin content in the feed.

The fluidizing gas velocity through the catalyst bed is 0.7 to 1.3 ft/sec and comprises light olefin feed and the hydrocarbon conversion products. Catalyst particles are disengaged from hydrocarbon gas products in the top dilute phase of the reaction zone in solid separation cyclones 8 and 9 and the catalyst is returned to the fluidized bed reaction zone through dip legs 8A and 9A. The hydrocarbon product gas is removed from the top of the reactor for further processing through outlet line 10.

The weight hourly space velocity and uniform contact in the reactor fluidized bed reaction zone 5 provides a close control of contact time between vapor or vapor and liquid and solid phases of about 3–25 seconds.

The catalytic oligomerization conversion reaction converts a minor portion of the light olefin hydrocarbon feed to coke by-products which coke deposits on the catalyst and partially deactivates the catalyst as the coke deposits build up. Also, during the reaction hydrocarbon product is absorbed on the catalyst which if not removed can represent a loss of product yield for the process.

In order to regenerate the catalyst and to recover the absorbed hydrocarbon product, a portion of the partially deactivated catalyst containing the deposited coke and absorbed hydrocarbon product is continuously withdrawn from the fluidized bed portion of the reactor and transferred by catalyst outlet means 11 through valve control means 11A to catalyst stripper vessel 12. About 10 to 15 wt. %/hr of the catalyst inventory in the reactor is withdrawn for stripping and regeneration.

The catalyst is withdrawn from the reactor at about the reaction zone temperature and pressure and is fed to the stripper vessel. The partially deactivated catalyst contains 1 to 3 wt. % coke and 0.1 to 1.0 wt. % absorbed hydrocarbon product, based on weight of catalyst.

The partially deactivated catalyst is maintained as a fluid bed in the stripper zone 13 at a temperature of 500° to 700° F. (260° to 370° C.) and at about the same pressure as the reactor and is contacted in the stripper zone 13 with an inert stripping gas such as nitrogen. The nitrogen stripping gas is introduced into the bottom of the stripping zone through line 14 and distribution plate 15 at a temperature of 50° to 100° F. (10° to 38° C.) and at a sufficient rate to maintain the fluidized bed in stripping zone 13 and to maintain a stripping gas velocity through the fluidized bed of 0.5 to 1.5 ft/sec (0.15 to 0.45 m/sec). The partially deactivated catalyst in the stripping zone is stripped of substantially all of the hydrocarbon product, leaving on the catalyst substantially only deposited coke. The deposited coke constitutes about 1 to 3 wt. % of the catalyst. The stripped hydrocarbon product is returned to the reactor through outlet line 16 for recovery of the hydrocarbon.

The stripped catalyst containing deposited coke is withdrawn from the stripping zone through stripped catalyst outlet line 17 and valve control means 17A at a temperature of 500° to 700° F. (260° to 370° C.). The stripped catalyst is entrained in the air regeneration gas provided via line 18 and transported via riser 19 to the top portion of the regenerator vessel 20. The main portion of the regeneration gas is introduced into the regenerator 20 via line 21 and distributor plate 22 to effect fluidization of the stripped catalyst in the fluidized bed 23 of the regeneration zone.

The partially deactivated catalyst is contacted in the fluidized bed of the regenerator 20 with an oxygen containing regeneration gas such as air to effect combustion of the coke and removal of the coke from the catalyst and regeneration of the catalyst. A sufficient amount of the oxygen containing regenerating gas is fed to the regeneration zone via line 21 and distribution plate 22 to maintain the catalyst as a fluidized bed. The temperature in the fluidized bed is maintained at 900° to 950° F. (480° to 510° C.) by controlling the amount of oxygen containing gas introduced to the regeneration zone and by controlling the amount and temperature of the saturated steam coolant water fed to cooling coil 31. The water partial pressure in the regenerator is maintained at 5 to 10 psia. The pressure in the regenerator is about the same as in the reactor, e.g. about 150 to 200 psig (1130 to 1470 KPa) and is maintained by pressurizing the regeneration gas fed through line 24 in compressor 25 prior to introducing it into the regenerator. The pressurized air regeneration gas can be cooled in heat exchange 60 and any condensed water removed in knock-out drum 62. The dry regeneration gas can then be heated in furnace 26 to obtain close control of the temperature in the regenerator zone especially during periods of low catalyst throughput.

The fluidizing gas velocity in the fluidized bed regeneration zone 23 is 0.5 to 1.5 ft/sec. The catalyst particles are disengaged from the fluidizing gas, including combustion products of the coke and oxidizing gas, in the top dilute phase 27 of the regenerator in cyclone separator 28. The separated catalyst is returned to the regeneration zone through dip leg 28A. The effluent gases containing 0 to 50 ppm carbon monoxide, 5 to 10 mol. % oxygen and 0.1 to 1.5 wt. % catalyst fines is withdrawn from the regenerator through effluent gas outlet line 29.

In order to maintain the regeneration zone fluidized bed within the desired temperature range boiler feed water (BFW) coolant is fed through line 30 to heat exchanger 33a in which it is heated by hot effluent hydrocarbon product gases fed to heat exchanger 33a through line 10. The saturated steam water coolant is heated in heat exchanger 33a to a temperature of 400° to 500° F. (236° to 260° C.) and is then fed the catalyst regenerator cooling coil 31 in the fluidized bed regeneration zone 23. The BFW water coolant becomes heated in the cooling coil 31, while cooling the catalyst regeneration zone and is removed from coil 31 via line 32 at the steam saturation temperature. The mixed steam-water stream leaving coil 31 is further heated by heat exchange in heat exchanger 33b with hot effluent hydrocarbon product gases in line 10. High pressure steam is removed from heat exchanger 33b via line 35 and taken for further use in the refinery or for off site use. The high pressure steam stream in line 35 can be superheated by the reactor effluent using an additional heat exchanger, not shown. The effluent product stream is withdrawn from the heat exchanger 33a via line 34 at a temperature of 420° to 720° F. and taken for further processing. A portion of the high pressure unvaporized boiler feed water (BFW) in heat exchanger 33b can be recycled to the BFW feed line 30 via pump 35b and line 35a.

The effluent gases from the catalyst regenerator in line 29 can conveniently be fed as regeneration gas to the FCC catalyst regenerator in which the carbon monoxide is converted to carbon dioxide, the excess oxygen is burned and the catalyst particles added to the FCC process to enhance the FCC reaction process.

The catalyst is regenerated in the regeneration zone 23 by the combustion and removal of substantially all of the coke deposited on the catalyst. The residence time of the catalyst in the regeneration zone is 30–60 minutes. The regenerated catalyst containing only a residual amount of carbon in the amount of 0.01 to 0.10 wt. % based on the weight of catalyst is continuously withdrawn from the regenerator through catalyst withdrawal line 36 via valve control means 36A and lifted to the catalyst bed through return riser conduit 7 with pressurized olefin feed fed through line 6 to catalyst return riser 7 and is contacted with fresh olefin feed in the fluidized bed reaction zone 5.

Since the amount of regenerated catalyst returned to the reactor is relatively small, the temperature of the regenerated catalyst does not upset the temperature constraints of the reactor operation in a significant amount.

The recovered hydrocarbon product from line 34 comprises $C_5+$ gasoline range and middle distillate range hydrocarbons and is thereafter processed as required to provide the desired gasoline range product or higher boiling distillate product.

Use of the process of the present invention to carry out the catalytic reaction under turbulent regime fluidized bed operating conditions are described in the Avidan et al U.S. Pat. No. 4,547,616 which is incorporated herein by reference. Typical production fractionation systems that can be used for the effluent hydrocarbon product are described in U.S. Pat. Nos. 4,456,799 and 4,504,693 (Owen et al).

The temperature can be controlled in the fluidized bed reactor by indirect heat exchange of a cooling coil, not shown, in the fluidized bed and/or by heating or cooling the olefin fed. Part or all of the reaction heat can be removed from the reactor by using cold feed, whereby reactor temperature can be controlled by adjusting feed temperature. The heat contained in the reaction product can as previously discussed be recovered in heat exchangers 33a and 33b by heat exchange with saturated steam coolant water, e.g. boiler feed water to make high pressure steam. The temperature in the stripping vessel 12 can be partially controlled by controlling the temperature of the nitrogen stripping gas.

Figure 2:
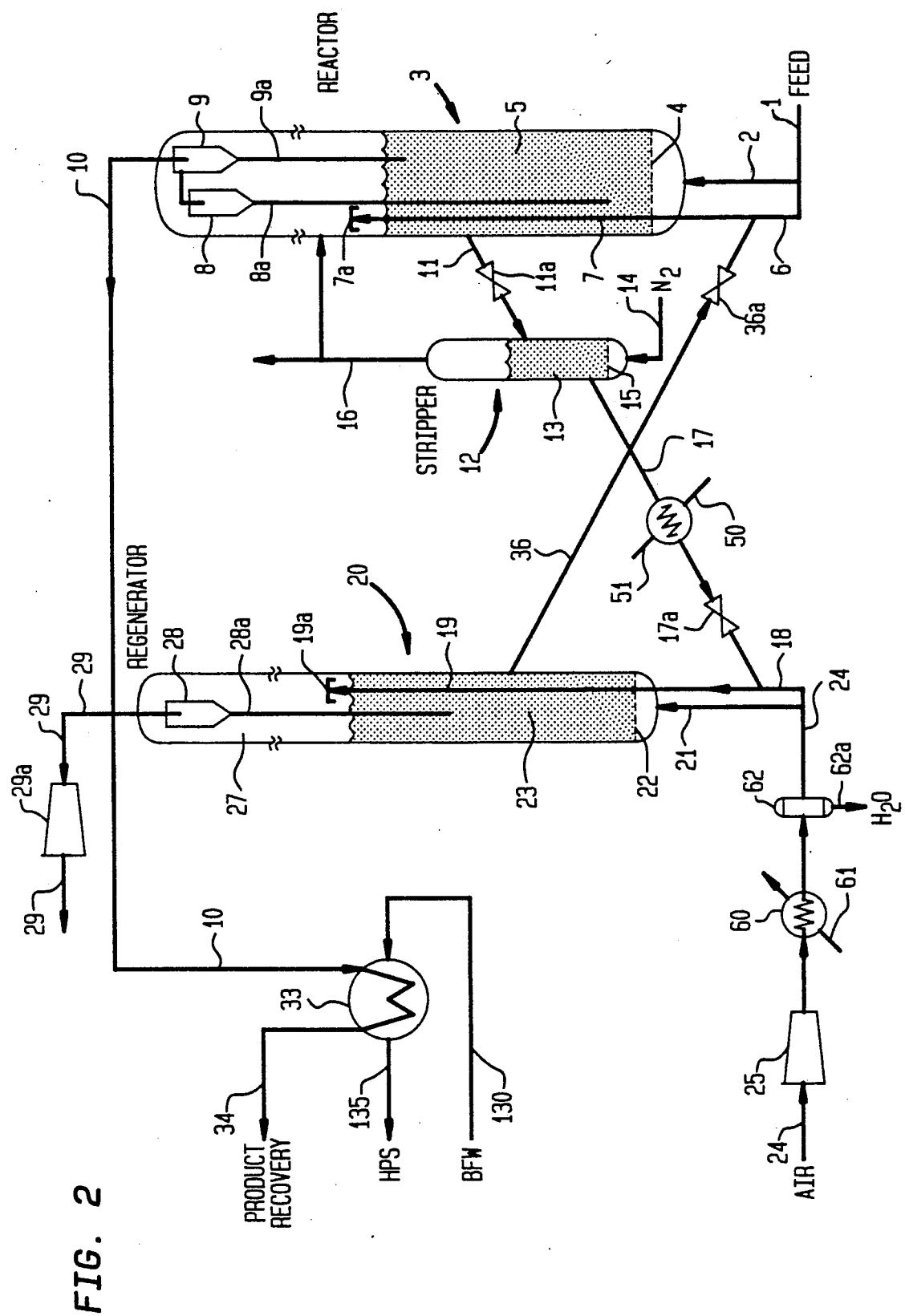

Another embodiment of the invention is illustrated in FIG. 2 of the drawings in which the same numbers represent the same items as in FIG. 1. In the FIG. 2 drawings the temperature in the regeneration zone 20 is controlled by cooling the catalyst withdrawn from the stripper vessel 12 and by cooling the oxygen containing regeneration gas prior to introduction to the regenerator. The hot effluent gases from the reactor are heat exchanged with boiler feed water (BFW) coolant water to make high pressure steam.

With reference to FIG. 2 of the drawings, the oligomerization reaction is carried out in the fluidized bed reaction zone at a temperature of 600° to 750° F. (316° to 399° C.) and at a pressure of 100 to 250 psig (790 to 1800 KPa). The light hydrocarbon feed is fed to the reactor at 0.5 to 1.5 WHSV, based on ethene, propene and butene content in the feed.

The fluidizing gas velocity through the catalyst bed is 0.7 to 1.3 ft/sec (0.2 to 0.4 m/sec) and comprises the light olefin feed and the hydrocarbon products.

The catalytic oligomerization conversion reaction converts a portion of the light olefin hydrocarbon feed to coke by-products which coke deposits on the catalyst partially deactivates the catalyst as the coke deposits build up.

In order to regenerate the catalyst and to recover the absorbed hydrocarbon product, a portion of the partially deactivated catalyst is continuously withdrawn from the fluidized bed portion of the reactor and transferred by catalyst outlet means 11 through valve means 11A to catalyst stripper vessel 12. About 10 to 15 wt. %/hr of the catalyst inventory in the reactor is withdrawn for stripping and regeneration. The catalyst is withdrawn from the reactor at the reaction temperature of 600° to 750° F. (316° to 399° C.) and at a pressure of 100 to 250 psig (790 to 1800 kPa). The partially deactivated catalyst contains 1 to 3 wt. % coke and 0.1 to 1 wt. % absorbed hydrocarbon product.

The stripped catalyst containing deposited coke is withdrawn through outlet line 17 at a temperature of 500° to 700° F. (260° to 370° C.) and is cooled in heat exchanger 50 by indirect contact with a cooling fluid, e.g. steam. The cooled catalyst is fed through valve control means 17A at a temperature of 100° to 200° F. (38° to 93° C.) to the catalyst regeneration vessel 20.

The fluidized bed catalytic reactor and the stripper vessel are otherwise operated as in the FIG. 1 embodiment.

The oxygen containing regeneration gas, for example air, prior to introduction in the regenerator vessel 20 is fed through line 24 to compressor 25 and pressurized to a pressure of 150 to 200 psig (1130 to 1470 KPa) and contacted and cooled in heat exchanger 60 with a cooling fluid, e.g. steam, to reduce the temperature of the regenerating gas to 80° to 120° F. (27° to 49° C.). The pressurized and cooled regeneration gas is fed to knock out drum 62 in which any condensed moisture (water) is removed through line 62A. The cooled and dried pressurized regeneration gas is fed through line 24 and line 18 and 21 to the regenerator vessel 20. The cooled stripped catalyst at a temperature of 100° to 200° F. (38° to 93° C.) is entrained in the regeneration gas provided via line 18 and transported via riser 19 to the top portion of the regenerator vessel 20. The main portion of the regeneration gas is introduced into the regenerator 20 via line 21 and distributor plate 22 to effect fluidization of the stripped catalyst in the fluidized bed of the regeneration zone 23.

The partially deactivated catalyst is contacted in the fluidized bed of the regenerator 20 with the cooled air regeneration gas to effect combustion of the coke and removal of the coke from the catalyst and regeneration of the catalyst. A sufficient amount of the cooled air regeneration gas is fed to the regeneration zone via line 21 and distribution plate 22 to maintain the catalyst fluidized. The temperature to which the regeneration air is cooled in heat exchange 60 is controlled to maintain the temperature in the regeneration zone 23 at 850° to 950° F. (454° to 510° C.). The pressure in the regeneration zone is maintained at 150 to 200 psig (1130 to 1470 KPa) by pressurizing the regeneration gas in compressor 25. The fluidizing gas velocity in the regeneration zone 23 is 0.5 to 1.5 ft/sec (0.15 to 0.46 m/sec). The catalyst particles are disengaged from the fluidizing gas, including combustion products of the coke and oxidizing gas, in the top dilute phase 27 of the regenerator in cyclone separator 28. The separated catalyst is returned to the regeneration zone through dip leg 28A. The water partial pressure in the regeneration zone is 5 to 10 psia. The effluent gases containing 0 to 50 ppm carbon monoxide, 5 to 20 mol. % oxygen and 0.1 to 1.5 wt. % catalyst fines is withdrawn through the regenerator 20 through effluent gas outlet line 29.

The heat in the hot effluent hydrocarbon product gases in line 10 from the reactor 3 is recovered by indirect heat exchange in heat exchanger 33 with saturated steam, e.g. boiler feed water (BFW) to produce high pressure steam and to cool the product gases.

The residence time of the catalyst in the regeneration zone is 30 to 60 minutes. The regenerated catalyst containing only a residual amount of carbon in the amount of 0.01 to 0.05 wt. % based on weight of catalyst is continuously withdrawn from the regenerator through catalyst withdrawal line 36 via valve control means 36A and lifted to the catalyst bed through return riser conduit 7 with pressurized olefin feed fed through line 6 to catalyst return riser 7 and is contacted with fresh olefin feed in the fluidized bed reaction zone 5.

In another embodiment of the invention the process is carried out in a riser reactor as illustrated in FIG. 3 of the drawings.

Referring to FIG. 3 of the drawings, a pressurized feed gas rich in $C_2$-$C_4$ olefins is fed through line 101 to the bottom of riser section 107 where it is contacted with regenerated catalyst fed to the riser reactor through catalyst return line 36 via flow control means 36a. The regenerated catalyst is lifted in the riser section 107 to fluidized catalyst bed section 105. The oligomerization conversion reaction takes place primarily in the riser section 107 which is maintained at a temperature of 600° to 750° F. (316° to 399° C.) and at a pressure of 100 to 250 psig (790 to 1800 kPa). The light hydrocarbon feed based on $C_2$ to $C_4$ olefin content is fed to the riser reactor at 2 to 8 WHSV. The transfer gas velocity in the riser section is maintained at 10 to 20 ft/sec (3 to 6.1 m/sec) and comprises the light olefin feed and the hydrocarbon products.

A portion of the catalyst in fluidized catalyst bed 105 can be recirculated through catalyst recirculation line 112 via flow control valve 113 to enter the bottom of riser reactor 107 and can be mixed with feed fed through line 101.

The catalyst residence time in the riser reactor is 3 to 10 sec. The catalyst particles are disengaged from the hydrocarbon gas products in the top dilute phase of the reactor in solid separation cyclones 108 and 109 and the catalyst returned to the fluidized bed reaction zone through dip legs 108A and 109A.

The partially deactivated catalyst is withdrawn from the reactor at about the reaction temperature and reaction pressure and fed to the catalyst stripper vessel 12. The partially deactivated catalyst contains 1 to 3 wt. % coke and 0.1 to 1 wt. % absorbed hydrocarbon product.

The withdrawn catalyst is stripped and regenerated generally following the procedure discussed above with reference to FIG. 1 of the drawings.

About 50 to 500 wt. %/hr of the catalyst inventory in the regenerator is recirculated.

The cooling of the regeneration zone 20 as shown in FIG. 3 is modified from that of FIG. 1 to produce superheated HPS. The regeneration zone fluidized bed temperature is maintained within the desired temperature range by feeding boiler feed water (BFW) coolant through line 30 to heat exchanger 33a in which it is heated by hot effluent hydrocarbon product gases fed to heat exchanger 33a through line 10. The heated coolant is then fed via line 30a to heat exchanger 33b in which it is further heated by hot effluent hydrocarbon product gases fed to heat exchanger 33b through line 10. The thus heated coolant is then fed through line 135 to the catalyst regenerator cooling coil 31 in the fluidized bed regeneration zone 23. The BFW water coolant is further heated in the cooling coil 31, while cooling the catalyst regeneration zone and is removed from coil 31 via line 132 as superheated HPS. The superheated HPS in line 132 is taken for further use in the refinery or for off site use.

The effluent product stream is withdrawn from the heat exchanger 33a via line 34 and taken for further processing.

The present invention is further exemplified by the following Examples.

EXAMPLE 1

The process is carried out in a fluid bed reactor using HZSM-5 catalyst comprising a weight ratio of catalyst to silica alumina binder of 25/75.

The process is carried out using a FCC $C_2$ to $C_4$ light olefin gas feed.

The composition of the light olefin feed is as follows:

| Feed Gas | Mole % |
| --- | --- |
| Hydrogen | 19.1 |
| Inert gases | 11.7 |
| Methane and Ethane | 32.0 |
| Ethene | 10.0 |
| Propene | 16.0 |
| Propane | 6.0 |
| Butene | 1.8 |
| Butane | 1.4 |

| -continued | |
|---|---|
| Feed Gas | Mole % |
| $C_5^+$ | 2.0 |

The process is carried out using the FIG. 1 embodiment of the invention. The feed is fed at about 0.8 WHSV based on olefins and contacted with the HZSM-5 catalyst in the fluidized bed of the reactor under oligomerization conditions of a temperature of about 850° F. (454° C.) and a pressure of about 175 psig (1300 KPa). The single pass conversion of the ethene and propene in the feed is 94 and 95% respectively. The catalyst residence time in the reactor is 8 hours. About 12.5% of the reactor catalyst inventory per hour is withdrawn for stripping and regeneration.

The partially deactivated catalyst containing about 2.4 wt. % coke and 0.2 wt. % absorbed hydrocarbon product is continuously withdrawn from the reactor. The withdrawn catalyst is introduced into a catalyst stripper and contacted in the catalyst stripper in a fluidized bed stripping zone at a temperature of about 800° F. (425° C.) and pressure of about 175 psig (1300 KPa) with nitrogen stripping gas. The catalyst residence time in the stripper is about 100 seconds. The stripped catalyst having substantially all of the hydrocarbon product removed and containing 2.4 wt. % coke is continuously withdrawn from the stripping zone and fed to the catalyst regenerator.

The stripped catalyst is maintained as a fluidized bed in the regenerator by the introduction of compressed air regenerating gas at a pressure of about 175 psig (1300 KPa) and a temperature of about 200° F. (93° C.).

The pressure in the regeneration zone is maintained by pressurizing the regeneration gas prior to introducing it into the regeneration zone. The water partial pressure in the regeneration zone is about 10–15 psia.

The regeneration gas is introduced at a sufficient rate to burn substantially all of the coke from the catalyst. The temperature in the regeneration zone is maintained at the desired level of 935° F. (500° C.) by withdrawing heat from the regeneration zone through cooling coils maintained in the fluidized bed in the regeneration zone. A cooling fluid such as boiler feed water (BFW) is fed to the cooling coils at a temperature of about 450° F. (232° C.) and withdrawn at a temperature of about 650° F. (343° C.).

The boiler feed water cooling fluid is preferably preheated by heat exchange with the reactor effluent as shown in FIG. 1. The cooling fluid is preheated to a temperature of for example 450° F. The regenerated catalyst contains about 0.05 wt. % residual carbon and is fed to the reactor with fresh olefin feed.

The effluent gas from the regenerator contains a maximum of 50 ppm CO, about 12.4 mol % oxygen (13.7 wt. % oxygen) about 5 to 9 mol % water (3.7 wt. % water).

The above Example 1 shows that the process of the present invention can be carried out and the catalyst effectively regenerated in the regenerator at a temperature of 935° F. and pressure of 175 psig, and water partial pressure of 10–15 psia. The regeneration step is effective in regenerating the catalyst and in reducing the residual carbon content of the catalyst to about 0.05 wt. % without damage to the catalyst.

The Example further shows the utilization of the inert gas stripping step and the cooling coil in the catalyst regenerator provide an efficient and effective process for regeneration of the catalyst at low temperature and low water partial pressure in the regeneration zone whereby the catalyst activity and catalyst life are increased.

EXAMPLE 2

The process is carried out following the procedure and process conditions of Example 1, with the exception that there are no cooling coils in the catalyst regenerator.

Without the cooling effect of the cooling coils, the catalyst regeneration temperature increases to about 1185° F. (640° C.), which results in damage to the catalyst and significantly shortening of the useful life of the catalyst.

EXAMPLE 3

The process is again carried out following the procedure and process conditions of Example 1, with the exception that the catalyst stripping step is omitted. The omission of the catalyst stripping step results in the hydrocarbons that are absorbed on the catalyst during the oligomerization reaction being carried over into the catalyst regenerator. It is found that in order to maintain the regeneration temperature under these conditions at about the desired 935° F. (500° C.), regeneration temperature, it is necessary to increase the heat duty removal capacity of the cooling coils by 20–40%.

Having thus generally described the present invention and discussed the preferred embodiments in support thereof, it is to be understood that no undue restrictions are to be imposed by reason thereof except as defined by the following claims.

What is claimed is:

1. A process for the conversion of light olefins to heavier hydrocarbons which comprises contacting light olefin feed in a fluidized catalyst reactor reaction zone with a shape selective medium pore molecular sieve zeolite catalyst under oligomerization conditions at a temperature of 400° to 950° F. and at a pressure of 100 to 400 psig to convert the light olefin feed to heavier hydrocarbon product and to coke by-product, the coke by-product deposits on the catalyst to partially deactivate the catalyst and a portion of the hydrocarbon product is absorbed on the catalyst, withdrawing and recovering hydrocarbon product from the reaction zone, withdrawing partially deactivated catalyst containing coke and absorbed hydrocarbon product from the reaction zone and transferring the withdrawn catalyst to a catalyst stripping zone, contacting the partially deactivated catalyst in the stripping zone, at a temperature of 300° to 750° F. and at a pressure within 20 psi of the pressure in the reactor, with an inert stripping gas to strip and remove substantially all of the absorbed hydrocarbon product from the catalyst, withdrawing stripped catalyst containing deposited coke from the stripping zone and transferring the withdrawn catalyst to a catalyst regeneration zone in which a fluidized bed of catalyst is maintained, contacting the catalyst in the fluidized bed, at a temperature of 700° to 1000° F. and at a pressure within 20 psi of the pressure in the reactor and a water partial pressure of 1 to 20 psia, with an oxygen containing regeneration gas to effect combustion of the coke and removal of a substantial proportion of the coke from the catalyst and a regeneration of the catalyst, said regenerated catalyst containing a minor 0.01 to 0.5 wt. % amount of residual carbon, and withdrawing hot effluent gas from the regeneration zone and withdrawing regenerated catalyst from the regeneration zone and introducing said withdrawn regenerated catalyst to the reaction zone and contacting the regenerated catalyst in the reaction zone with fresh light olefin feed.

2. The process of claim 1 wherein the stripping zone pressure is about the same as the reactor pressure.

3. The process of claim 1 wherein the water partial pressure in the regeneration zone is 5-15 psia and the regenerated catalyst contains 0.01 to 0.05 wt. % of residual carbon.

4. The process of claim 1 wherein the hot effluent gas from the regeneration zone contains catalyst fines, CO and excess oxygen.

5. The process of claim 1 wherein the regenerated catalyst introduced to the reaction zone contains 0.01 to 0.2 wt. % residual carbon.

6. The process of claim 1 wherein the oxygen containing regeneration gas is passed through a compressor to increase its pressure prior to feeding the regeneration gas to the regeneration zone, and the hot effluent gas from the regenerator is passed through an expansion turbine to generate power to operate the compressor.

7. The process of claim 1 wherein the hot effluent gas from the regeneration zone contains catalyst fines, CO and excess oxygen and the effluent gas is passed to a Fluid Catalytic Cracking (FCC) catalyst regeneration zone.

8. The process of claim 1 wherein the oxygen containing regeneration gas fed to the regeneration zone is obtained from the regeneration gas feed to a Fluid Catalytic Cracking (FCC) catalyst regenerator.

9. The process of claim 1 wherein the regeneration zone comprises a cooling coil and a sufficient amount of a coolant fluid is passed through the cooling coil to maintain the temperature in the regeneration zone.

10. The process of claim 1 wherein the regeneration zone comprises a cooling coil and a sufficient amount of boiler feed water coolant is passed through the cooling coil to maintain the temperature in the regeneration zone.

11. The process of claim 10 wherein the boiler feed water prior to introduction to the cooling coil is heat exchanged in a first heat exchanger with hot effluent hydrocarbon product gas from the reactor, the boiler feed water in the cooling coil is at least partially converted to high pressure steam and the at least partially converted boiler feed water is heat exchanged in a second heat exchanger with hot effluent hydrocarbon product gas from the reactor and the high pressure steam is removed for further use.

12. The process of claim 1 wherein the regeneration zone comprises a cooling coil and a sufficient amount of high pressure saturated steam generated by indirect heat exchange with the reactor effluent is superheated by being passed through the cooling coil to maintain the temperature in the regeneration zone.

13. The process of claim 1 wherein the oxygen containing regeneration gas is cooled, and its free water content is removed, prior to being fed to the regenerator such that it maintains the temperature and water partial pressure in the regeneration zone.

14. The process of claim 1 wherein the catalyst regeneration is conducted with a regeneration gas containing 1 to 20% excess oxygen.

15. The process of claim 1 wherein the oxygen containing regeneration gas is preheated prior to being fed to the regeneration zone to control the regeneration zone temperature within the range.

16. The process of claim 1 wherein the reactor is a fluidized bed reactor.

17. The process of claim 1 wherein the reactor zone pressure and the regeneration zone pressure are about the same.

18. The process of claim 1 wherein the reaction zone pressure and the regeneration zone pressure are about the same and are within the range of 100 to 250 psig.

19. The process of claim 1 wherein the reaction zone pressure, the stripper zone pressure and the regeneration zone pressure are about the same.

20. A process for the conversion of light olefins to heavier hydrocarbons which comprises contacting light olefin feed in a fluidized catalyst reactor reaction zone with a shape selective medium pore molecular sieve zeolite catalyst under oligomerization conditions of a temperature of 500° to 750° F. and a pressure of 100 to 400 psig to convert the light olefin feed to heavier hydrocarbon product and to coke by-product, the coke by-product deposits on the catalyst to partially deactivate the catalyst and a portion of the hydrocarbon product is absorbed on the catalyst, withdrawing and recovering hydrocarbon product from the reaction zone, withdrawing partially deactivated catalyst containing coke and 0.1 to 1.5 wt. % absorbed hydrocarbon product from the reaction zone and transferring the withdrawn catalyst to a catalyst stripping zone, contacting the partially deactivated catalyst in the stripping zone, at a temperature of 300° to 750° F. and at a pressure within 20 psi of the pressure in the reactor, with an inert stripping gas to strip and remove substantially all of the absorbed hydrocarbon product from the catalyst, withdrawing stripped catalyst containing 1 to 4 wt. % deposited coke from the stripping zone and transferring the withdrawn catalyst to a catalyst regeneration zone in which a fluidized bed of catalyst is maintained, contacting the catalyst in the fluidized bed, at a temperature of 850° to 950° F. and at a pressure of 100 to 250 psig and at a water partial pressure of 1 to 15 psia, with an oxygen containing regeneration gas to effect combustion of the coke and removal of a substantial proportion of the coke from the catalyst and regeneration of the catalyst, said regenerated catalyst containing a minor 0.01 to 0.20 wt. % amount of residual carbon, and withdrawing hot effluent gas from the regeneration zone and withdrawing regenerated catalyst from the regeneration zone and introducing said withdrawn regenerated catalyst to the reaction zone and contacting the regenerated catalyst in the reaction zone with fresh light olefin feed.

21. The process of claim 20 wherein the stripping zone pressure is about the same as the reactor pressure.

22. The process of claim 20 wherein the regeneration pressure is within 20 psi of the reactor pressure.

23. The process of claim 20 wherein the catalyst regeneration is conducted with a regeneration gas containing 1 to 20% excess oxygen.

24. The process of claim 20 wherein the reactor zone pressure and the regeneration zone pressure are about the same.

25. The process of claim 20 wherein the reaction zone pressure and the regeneration zone pressure are about the same and are within the range of 100 to 250 psig.

26. The process of claim 20 wherein the reaction zone pressure, the stripper zone pressure and the regeneration zone pressure are about the same.

27. A process for the conversion of light olefins to heavier hydrocarbons which comprises contacting light olefin feed in a fluidized catalyst reactor reaction zone with a shape selective medium pore ZSM-5 molecular sieve zeolite catalyst under oligomerization conditions of a temperature of 600° to 750° F. and a pressure of 100 to 250 psig to convert the light olefin feed to heavier hydrocarbon product and to coke by-product, the coke by-product deposits on the catalyst to partially deactivate the catalyst and a portion of the hydrocarbon product is absorbed on the catalyst, withdrawing and recovering hydrocarbon product from the reaction zone, withdrawing partially deactivated catalyst containing coke and 0.1 to 1.5 wt. % absorbed hydrocarbon product from the reaction zone and transferring the withdrawn catalyst to a separate catalyst stripper, contacting the partially deactivated catalyst in the stripping zone at a temperature of 500° to 750° F. and at about the same pressure as the reactor with an inert nitrogen stripping gas to strip and remove substantially all of the absorbed hydrocarbon product from the catalyst, withdrawing stripped catalyst containing 1 to 4 wt. % deposited coke from the stripping zone and transferring the withdrawn catalyst to a catalyst regeneration zone in which a fluidized bed of catalyst is maintained, contacting the catalyst in the fluidized bed, at a temperature of 850° to 950° F. and at about the same pressure as the reactor and at a water partial pressure of 1 to 15 psia, with an oxygen containing regeneration gas to effect combustion of the coke and removal of a substantial proportion of the coke from the catalyst and regeneration of the catalyst, said regenerated catalyst containing a minor 0.01 to 0.05 wt. % amount of residual carbon, and withdrawing hot effluent gas from the regeneration zone and withdrawing regenerated catalyst from the regeneration zone and introducing said withdrawn regenerated catalyst to the reaction zone and contacting the regenerated catalyst in the reaction zone with fresh light olefin feed.

28. The process of claim 20 wherein the oxygen containing regeneration gas fed to the regeneration zone is obtained from the regeneration gas feed to a Fluid Catalytic Cracking (FCC) catalyst regenerator.

29. The process of claim 27 wherein the oxygen containing regeneration gas is cooled, and its free water content is removed, prior to being fed to the regenerator such that it maintains the temperature and water partial pressure in the regeneration zone.

30. The process of claim 20 wherein the reactor is a riser reactor.

* * * * *